(12) United States Patent
Bershteyn et al.

(10) Patent No.: US 8,470,344 B2
(45) Date of Patent: Jun. 25, 2013

(54) AQUEOUS DISPERSIONS AND SOLUTIONS OF DIFFICULT TO DISSOLVE MATERIALS AND METHODS OF THEIR PREPARATION

(75) Inventors: Yosef Bershteyn, Pardes Hana (IL); Anna Faingersh, Hadera (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 1845 days.

(21) Appl. No.: 11/433,013

(22) Filed: May 12, 2006

(65) Prior Publication Data

US 2007/0134278 A1 Jun. 14, 2007

Related U.S. Application Data

(60) Provisional application No. 60/749,244, filed on Dec. 9, 2005.

(51) Int. Cl.
*A61K 9/00* (2006.01)
*A61K 9/14* (2006.01)
*A61K 9/16* (2006.01)
*A61K 31/535* (2006.01)

(52) U.S. Cl.
USPC ........... 424/400; 424/484; 424/489; 424/490; 514/236.2

(58) Field of Classification Search
USPC ............... 424/400, 484, 489, 490; 514/236.2
See application file for complete search history.

(56) References Cited

U.S. PATENT DOCUMENTS

| 6,297,240 B1 * | 10/2001 | Embleton | 514/236.2 |
| 6,395,300 B1 * | 5/2002 | Straub et al. | 424/489 |
| 2004/0022844 A1 | 2/2004 | Hasenzahl et al. | |
| 2005/0228048 A1 * | 10/2005 | Asada et al. | 514/561 |

FOREIGN PATENT DOCUMENTS

| EP | 1 275 377 A1 | 1/2003 |
| EP | 1 532 981 A1 | 5/2005 |
| WO | WO 03/063835 A1 | 8/2003 |
| WO | WO 2004024164 A1 * | 3/2004 |
| WO | WO 2004/075817 A2 | 9/2004 |

OTHER PUBLICATIONS

Leuner et al., European Journal of Pharmaceutics and Biopharmaceutics, 2000, 50, 47-60.*
European Search Report, issued Oct. 4, 2006, for European Patent Application No. 06252582.9, filed May 12, 2006.

* cited by examiner

*Primary Examiner* — Abigail Fisher
(74) *Attorney, Agent, or Firm* — Kenyon & Kenyon LLP

(57) ABSTRACT

The present invention encompasses a method of preparing a ready-to-dissolve or ready-to-disperse composition of difficult to dissolve in water compounds and suspensions or aqueous solutions of difficult to dissolve in water compounds.

17 Claims, No Drawings

US 8,470,344 B2

AQUEOUS DISPERSIONS AND SOLUTIONS OF DIFFICULT TO DISSOLVE MATERIALS AND METHODS OF THEIR PREPARATION

RELATED APPLICATIONS

This application claims the benefit of U.S. Provisional Application No. 60/749,244, filed Dec. 9, 2005.

FIELD OF THE INVENTION

The invention encompasses aqueous dispersions and saturated solutions of water insoluble or slightly soluble compounds and methods of preparing the same.

BACKGROUND OF THE INVENTION

The human body is approximately 80% water; thus, it is advantageous to administer aqueous solutions of drugs to patients. However, not all compounds or drugs are easy to dissolve in water and often this is due to their poor solubility. Some compounds are slightly water soluble and others are not water soluble at all. Often this lack of solubility is compounded by further difficulties in forming a solution due to the physical nature of the materials for example their being viscous, glue-like or heat sensitive. Compounds that are not water soluble or slightly soluble may be soluble in organic solvents. Solutions of these compounds in organic solvents, however, may not be convenient for a variety of reasons. For example, regulatory authorities may limit the amount of organic solvents within a formulation to be administered to patients, or the organic solvents may be toxic. Therefore, while the preparation of aqueous solutions or suspensions of difficult to dissolve in water compounds is important in the field of drug delivery, many active pharmaceutical ingredients may not be available as solutions because they are water insoluble compounds. An example of a difficult to dissolve in water drug that must be solubilized prior to administration is latanoprost, which is used in ophthalmic solutions.

Traditionally, difficult-to-dissolve-in-water compounds that were intended to be formulated as dispersions or solutions were heated together with water to increase dissolution and facilitate solubility. A compound to be dissolved and water were often mixed and this mixture then heated to promote dissolution. After cooling the mixture to the desired temperature a solution or a dispersion of the substance in saturated solution could be obtained. A saturated solution could be obtained if any undissolved material was removed. This method, however, is ineffective where the compound to be dissolved is viscous and glue-like or heat sensitive. Viscous substances often stick to the walls of the vessel used to dissolve it or may agglomerate during cooling. For at least these reasons, solutions of difficult to dissolve compounds often can not even reach the theoretically possible concentrations and may even have difficulty being well-dispersed throughout the solution. Heating a slightly insoluble or insoluble compound is also inappropriate where the compound to be dissolved degrades upon heating. Moreover, this method is ineffective where the solubility of the compound to be dissolved is only slightly affected by an increase in temperature or not at all.

Therefore, the present invention addresses the deficiencies of the prior art. The invention encompasses methods for preparing suspensions or dispersions or aqueous solutions of difficult to dissolve in water or insoluble in water compounds, which can be applied to a variety of compounds without requiring heating to promote dissolution.

SUMMARY OF THE INVENTION

One embodiment of the invention encompasses methods for preparing ready-to-dissolve or ready-to-disperse composition of a difficult to dissolve in water compound comprising at least one substrate covered with at least one difficult to dissolve in water compound. The method for making the composition comprises preparing a solution of at least one difficult to dissolve in water compound in at least one solvent effective to dissolve the compound; covering the surface of at least one substrate, preferably a substrate that is insoluble in the solvent but soluble in water, with the solution to form a matrix; and removing the solvent.

Another embodiment of the invention encompasses methods for preparing an aqueous solution or suspension of difficult to dissolve in water compound comprising preparing a solid matrix by the method described above and combining the solid matrix with a sufficient amount of water to form an aqueous solution or suspension of the difficult to dissolve compound.

Another embodiment of the invention encompasses a method for preparing a suspension (dispersion) or aqueous solution of a difficult to dissolve in water compound comprising preparing a solution of at least one difficult to dissolve in water compound in at least one solvent effective to dissolve the compound; covering the surface of at least one substrate, preferably a substrate that is insoluble in the solvent but soluble in water, with the solution to form a matrix; and removing the solvent; and dissolving the resultant matrix in a sufficient amount of water to form a suspension or aqueous solution.

Typically, the solvent effective to dissolve the compound will be an organic solvent and preferably a volatile organic solvent. Optionally, the method further comprises adding at least one additional compound selected from the group consisting of buffers, coloring agents, emulsifying agents, flavoring agents, preservatives, solubilizers, surfactants, suspending agents, tonicity agents, and viscosity agents. Where the solutions or dispersions are to be used as ophthalmic solutions, the additional compound may be e.g. benzalkonium chloride and/or sodium chloride.

An embodiment of the invention is the matrix of the substrate covered with a difficult to dissolve material that will readily dissolve on introduction to water to achieve an aqueous solution or a dispersion of the difficult to dissolve material in a saturated solution of the difficult to dissolve material in water.

A particular embodiment of the invention is a ready-to-dissolve solid composition of latanoprost comprised of a water soluble substrate or substrates covered with latanoprost that upon introduction to a suitable amount of water will achieve saturation concentration. In most preferred forms of this embodiment the substrate or substrates will in turn comprise the excipient ingredients that are required for an ophthalmic solution so that upon dissolution, the resultant ophthalmic latanoprost solution is fully compounded.

In one embodiment, the preferred volatile organic solvent is a $C_1$-$C_6$ alcohol, acetonitrile, $C_3$-$C_4$ ketone, $C_1$-$C_3$ halogenated solvent, $C_3$-$C_4$ ester, or a lower boiling hydrocarbon. Preferably, the volatile organic solvent is a $C_1$-$C_4$ alcohol, acetonitrile, acetone, chloroform, ethylacetate, or a $C_5$-$C_7$ lower boiling hydrocarbon. In one particular embodiment, the volatile organic solvent is ethanol or acetonitrile.

In another embodiment the substrate is a component of a buffer solution, a salt component of a biological solution, or an organic component that is soluble in water but insoluble in an organic solvent. The substrate may be ascorbic acid, boric acid, citric acid, salts of edetic acid, paraben esters, potassium or sodium lauryl sulfate, potassium or sodium salts of phosphoric acid, sodium chloride, benzalkonium chloride, potassium chloride, potassium bromide, potassium iodide, sucrose, fructose, lactose, dextrose, or ringer lactate. Alternatively, the substrate may be ascorbic acid, boric acid, citric acid, edetate calcium disodium, edetate disodium, methyl paraben, ethyl paraben, sodium lauryl sulfate, sodium phosphate, sodium dihydrogen phosphate, sodium hydrogen phosphate, sodium chloride, sodium bromide, sodium iodide, benzalkonium chloride, potassium chloride, potassium bromide, potassium iodide, potassium phosphate, potassium dihydrogen phosphate, potassium hydrogen phosphate, sucrose, fructose, lactose, dextrose, or ringer lactate. More preferably, the substrate is $NaH_2PO_4$ or $Na_2HPO_4$.

In yet another embodiment, the removing step is performed under reduced pressure.

In one particular embodiment, the difficult to dissolve in water compound is dexamethasone, fluticasone, hydrocortisone, latanoprost, mometasone, or travoprost. Preferably, the compound is latanoprost.

In one particular embodiment, the amount of water added during the dissolving step is not sufficient to dissolve all substance on the matrix and a suspension (dispersion) in saturated solution is obtained. In another particular embodiment, the amount of water added is sufficient to form a saturated aqueous solution.

Another embodiment of the invention encompasses a saturated aqueous solution of a difficult to dissolve in water compound prepared according to the method described above.

In one embodiment, the invention encompasses a ready-to-dissolve or ready-to-disperse composition of a difficult to dissolve compound comprising at least one substrate covered with at least one difficult to dissolve compound. In one particular embodiment, the substrate is a mixture of $NaH_2PO_4$ and $Na_2HPO_4$ and the difficult to dissolve compound is latanoprost. In another particular embodiment, the substrate is $NaH_2PO_4 \cdot H_2O$ and the difficult to dissolve compound is dexamethasone.

Another embodiment of the invention encompasses a 0.005% (w/v) solution of latanoprost prepared according to the method described above, having a residual organic solvent content of less than about 20 μg/mL.

DETAILED DESCRIPTION OF THE INVENTION

The present invention encompasses suspensions (dispersions) or saturated aqueous solutions of difficult to dissolve in water compounds and methods of preparing the same. In particular, the invention encompasses compositions used to prepare suspensions or saturated solutions of difficult to dissolve in water compounds and suspensions or saturated aqueous solutions of difficult to dissolve in water compounds. Not to be limited by theory, however, it is believed that the dissolution kinetics of the difficult to dissolve in water compounds improves when the compound is dispersed upon the surface of a water soluble matrix. Consequently, in one embodiment, the present invention improves the dissolution of the compound at room temperature with a minimal amount of mixing.

As used herein, unless otherwise defined, a "difficult to dissolve in water compound" includes water insoluble compounds or compounds where their dissolving process is limited or impeded by other origins. For example, a water insoluble compound would have a water solubility of 5 mg/mL or less, preferably 2 mg/mL or less, and more preferably, 1 mg/mL or less. Other compounds that may be difficult to dissolve in water include those which are very viscous or glue-like. The invention apparently best displays its utility when the water insoluble compounds used in the invention are glue-like viscous substances or substances which degrade upon heating. Examples of water insoluble compounds include, but are not limited to, latanoprost, travoprost, fluticosone, dexamethasone, or hydrocortisone.

As used herein, unless otherwise defined, the term "suspension" or "suspensions" also include dispersions.

As used herein, unless otherwise defined, the term "aqueous solutions" includes aqueous solutions and saturated aqueous solutions.

A method of making a suspension or aqueous solution of a difficult to dissolve in water compound comprises dissolving a ready-to-dissolve or ready-to-disperse composition of matrix of a substrate and a difficult to dissolve in water compound in a sufficient amount of water to form a suspension or saturated aqueous solution.

A method for preparing ready-to-dissolve or ready-to-disperse composition of a difficult to dissolve in water compound comprises preparing a solution of at least one difficult to dissolve in water compound in at least one solvent effective to dissolve the compound; and covering the surface of at least one substrate with the solution to form a matrix. Preferably, the substrate is insoluble in the solvent but soluble in water.

The method of producing the desired suspension or aqueous solution comprises simply dissolving the matrix in water with minimal mixing to obtain the desired suspension or aqueous solution.

The method for making a suspension or aqueous solution may be carried out in one step and comprises preparing a suspension or aqueous solution of at least one difficult to dissolve in water compound, in at least one solvent; covering the surface of at least one substrate with the solution to form a matrix; removing the solvent to achieve a solid matrix; and dissolving the matrix in water with minimal mixing to obtain the suspension or aqueous solution.

Optionally, the method further comprises adding at least one compound to the solvent solution including, but are not limited to, buffers, tonicity agents, solubilizers, preservatives, viscosity agents, coloring agents, flavoring agents, and the like.

The solution of at least one difficult to dissolve in water compound and at least one preferably, volatile organic, solvent is prepared by mixing the difficult-to-dissolve-in-water compound in a sufficient amount of the solvent or solvents to obtain a solution. One of skill in the art with little or no experimentation can determine the amount of solvent necessary to dissolve the water insoluble compound. For example, the skilled artisan understands that factors such as amount, time, temperature, and the water insoluble compound itself may influence the amount of solvent necessary to form a solution. Preferably, the solution is homogeneous; however, this is not necessary. If minimal amounts of the water insoluble compound are still present, they may be removed by filtration or other means as is commonly known to the skilled artisan.

The preferred volatile organic solvent is at least one organic solvent where difficult to dissolve in water compound is soluble. As used herein, the term "volatile organic solvent" includes an organic solvent that is readily evaporated at atmospheric pressure or under reduced pressure, preferably without heating. If evaporated under reduced pressure, the solvent may be gently heated, as long as the amount of heat does not decompose the difficult to dissolve in water compound. For example, volatile organic solvents have a boiling point of about 120° C. or less, preferably the volatile organic solvents have a boiling point of about 100° C. or less, and more preferably, the volatile organic solvents have a boiling point of 85° C. or less.

Volatile organic solvents include, but are not limited to, a $C_1$-$C_6$ alcohol, acetonitrile, $C_3$-$C_4$ ketone, $C_1$-$C_3$ halogenated solvent, $C_3$-$C_4$ alkyl ester, or a $C_5$-$C_8$ lower boiling hydrocarbon. Preferably, volatile organic solvents include a $C_1$-$C_4$ alcohol, acetonitrile, acetone, chloroform, ethyl acetate, or a $C_5$-$C_7$ lower boiling hydrocarbon. $C_1$-$C_3$ halogenated solvents include, but are not limited to, mono-, di-, and/or tri-halogenated alkanes. $C_1$-$C_6$ Alcohols include, but are not limited to, methanol, ethanol, 1-propanol, 2-propanol, 1-butanol, 2-butanol, tert-butanol, 1-pentanol, 2-pentanol, 3-pentanol, and 1-hexanol. $C_5$-$C_7$ Lower boiling hydrocarbons include, but are not limited to, pentanes or hexanes. Preferred solvents are ethanol and acetonitrile.

Typically, difficult to dissolve in water compound include insoluble compounds that have a maximum water solubility of about 5 mg/mL or less, preferably of about 2 mg/mL or less, and more preferably, of about 1 mg/mL or less about 1 mg/mL or less and compounds that are difficult to dissolve due to the physical characteristics of the compound. Examples of difficult to dissolve in water compounds include, but are not limited to, dexamethasone, fluticasone, hydrocortisone, latanoprost, mometasone, or travoprost. It is understood that the term "difficult to dissolve in water compound" also includes any anhydrate and/or hydrate, and salt (hydrates of salts) of the compounds. For example, dexamethasone includes the dexamethasone acetate, dexamethasone sodium phosphate, and hydrates. Another example is hydrocortisone which includes hydrocortisone acetate, hydrocortisone butyrate, hydrocortisone hemisuccinate, hydrocortisone sodium phosphate, hydrocortisone sodium succinate, hydrocortisone valerate, and hydrates thereof.

The step of covering a surface of at least one substrate with the solution generally comprises covering or wetting the substrate with the solution. As used herein as applied to the substrate, the term "surface" includes an exterior surface and/or any interior surface that may be present such as in porous substrates. Thus, the substrate surface may be completely or partially covered. Typically, the solution is applied by spraying, dipping the substrate into the solvent, mixing the solution with the substrate, or any other method used to apply a solution to a substrate surface. The solvent solution may form a layer on the substrate surface or may only partially cover the surface or for that matter form droplets on the surface.

Compounds suitable as substrates include compounds that may be covered or coated with the solution and are water soluble. Typically, the substrate is a material that is soluble in water but insoluble in the solvent used to dissolve the difficult to dissolve in water compound. Typically, the substrate includes, but is not limited to, components of a buffer solution, salt components of biological solutions, or water soluble inorganic salts, organic components that are soluble in water but insoluble in organic solvents.

Components of a buffer solution include, but are not limited to, ascorbic acid, boric acid, citric acid salts, acetic acid salts, salts of hydrohalogenic acids, or salts of phosphoric acids. Salts of hydrohalogenic acids include, but are not limited to, sodium and/or potassium salts of hydrohalogenic acids. Salts of phosphoric acids include, but are not limited to, potassium or sodium hydrogen phosphate, potassium or sodium dihydrogen phosphate, potassium or sodium phosphate, including the anhydrous and hydrates (monohydrates, dihydrates, etc) forms thereof or for that matter mixtures of more than one. Salt components of biological solutions include, but are not limited to, edetic acid salts, sodium lauryl sulfate, chloride salts such as sodium chloride, sodium bromide, sodium iodide, or benzalkonium chloride, and potassium salts, such as potassium chloride, potassium bromide, or potassium iodide or mixtures thereof. The above list includes the salts in their anhydrous form, as well as the hydrate forms such as monohydrate, dihydrate, and trihydrate. For example, substrates include edetate calcium dihydrate or trihydrate, or edetate disodium dihydrate.

Organic components that are soluble in water include, but are not limited to, sugars, lactates, or paraben esters. Sugars include, but are not limited to, mannose, glucose, sucrose, fructose, lactose, or dextrose. Lactates include, but are not limited to, ringer lactate. Other organic components include methyl paraben, ethyl paraben, sorbitol or mannitol. It is understood that the substrate includes salts, anhydrates, hydrates (such as monohydrates, dihydrates, etc.) and solvates of the components described above.

The substrate may be at least one of ascorbic acid, boric acid, citric acid, salts of edetic acid, paraben esters, potassium or sodium lauryl sulfate, potassium or sodium salts of phosphoric acid, sodium chloride, benzalkonium chloride, potassium chloride, potassium bromide, potassium iodide, sucrose, fructose, lactose, dextrose, or ringer lactate. Preferred substrates include ascorbic acid, boric acid, citric acid, edetate calcium disodium, edetate disodium, methyl paraben, ethyl paraben, sodium lauryl sulfate, sodium phosphate, sodium hydrogen phosphate, sodium dihydrogen phosphate, sodium chloride, benzalkonium chloride, potassium chloride, potassium bromide, potassium iodide, sucrose, fructose, lactose, dextrose, or ringer lactate. More preferred substrates include sodium hydrogen phosphate, sodium dihydrogen phosphate, or their mixture.

In general it is of course apparent that the term "the substrate" need not be a single species but can be comprised of several components and they need not be of only one type as detailed above.

The removing step may be accomplished in a manner that removes the solvent from the matrix. Preferably, in the removing step where the solvent is a volatile organic solvent, sufficient volatile organic solvent is removed from the matrix to comply with maximum residual organic solvent as allowed by the FDA. Guidelines for the maximum residual organic solvent can be found in the FDA Inactive Ingredient Guide, FDA (Center for Drug Evaluation and Research, Division of Drug Information Resources, *Inactive Ingredient Guide*, October 2005) hereby incorporated by reference.

Typically, the preferably, volatile organic solvent is removed under reduced pressure, e.g. a pressure of less than 1 atmosphere, or by lyophilization. If heating is applied during the removing step, then the heat applied should be sufficient to remove the volatile organic solvent without degrading the difficult to dissolve in water compound. Preferably, the removing step is performed under reduced pressure and in the absence of heating.

The dissolving step comprises placing the matrix into a sufficient amount of water to form a solution or suspension. When creating a suspension, water is added to the matrix to dissolve the substrate, but the difficult to dissolve in water compound is present as a fine solid dispersion in a saturated solution. When preparing a solution, sufficient water may be added to form a saturated solution or, if desired, additional water may be added to dilute the solution up to target concentration. The dissolving step can be carried out using methods commonly known to the skilled artisan. With little or no experimentation, the skilled artisan can easily determine the amount of water necessary to form the suspension or solution taking into account factors such as amount of matrix, type of substrate, and the type of difficult to dissolve in water compound.

Optionally, the method further comprises adding at least one additional ingredient. Additional ingredients include, but are not limited to, buffers, coloring agents, emulsifying agents, flavoring agents, preservatives, solubilizers, surfactants, suspending agents, tonicity agents, or viscosity agents. Additional ingredient can be other pharmaceutical component or each other component of target formulation. Preferable additional ingredients for an ophthalmic solution or suspension include benzalkonium chloride and sodium chloride.

The following example illustrates the method of the invention. However, it should be understood that this is merely one example and not intended to limit the invention. The method of the invention is illustrated by way of example using the prostaglandin $F_{2\alpha}$ analogue (prostaglanoid selective FP receptor agonist)—latanoprost: Isopropyl (Z)-7-{(1R,2R,3R,5S)-3,5-dihydroxy-2-[3(R)-(3-hydroxyl-5-phenyl)pentyl] cyclopentyl}-5-heptenoate.

Typically, latanoprost is mixed with ethanol to form a solution. The solution is added to a mixture of $NaH_2PO_4$ and $Na_2HPO_4$ to yield a mixture. The mixture is dried under reduced pressure at room temperature to yield a dry powder having latanoprost on the surface. Subsequently, the dry powder is dissolved in water to yield a saturated aqueous solution of latanoprost 0.005% (w/v) with residual organic solvent content of less than about 20 µg/mL. The residual organic solvent content is significantly less than the maximum residual organic solvent content of 1.4% (14 mg/mL) permitted by the FDA. See FDA Inactive Ingredient Guide.

The invention also encompasses solutions or suspensions made using the method of the invention.

Having described the invention with reference to certain preferred embodiments, other embodiments will become apparent to one skilled in the art from consideration of the specification. The invention is further defined by reference to the following examples describing in detail the process and compositions of the invention. It will be apparent to those skilled in the art that many modifications, both to materials and methods, may be practiced without departing from the scope of the invention.

EXAMPLES

Example 1

1 mL of the Latanoprost solution (6.4 mg/mL) in ethanol was added to a mixture of $NaH_2PO_4*H_2O$ (0.553 g) and $Na_2HPO_4$ (0.564 g). The resulting mixture was dried under reduced pressure at room temperature to yield dry powder particles having latanoprost on the surface thereof. The dry powder was dissolved in water (120 mL) to form a solution. Benzalkonium chloride was added to the solution. The resultant solution was transparent and stable with a content of Latanoprost 0.005% (w/v). The residual ethanol content was found to be 0.6 µg/mL.

Example 2

Latanoprost (17.97 mg) was dissolved in acetonitrile (5 mL). 1.5 mL of this solution were added to mixture of $NaH_2PO_4$ (0.464 g) and $Na_2HPO_4$ (0.469 g). The resulting mixture was dried under reduced pressure to obtain a dry powder. 50 mL of water were added to dry powder and stirred during 5 minutes. A fine suspension of Latanoprost with concentration about 0.01% (w/v) was obtained. 50 mL of water, containing Benzalkonium chloride and sodium chloride, were added to this suspension and stirred. The obtained clear solution of Latanoprost had concentration 0.005% (w/v).

Example 3

Comparative Example

Latanoprost (5.621 mg) was dissolved in water (100 mL), containing $NaH_2PO_4$ (0.463 g). The mixture was stirred for 120 minutes. The aqueous solution only had a Latanoprost concentration of 0.00015% (w/v) or 30% of the target concentration of 0.005%.

Example 4

Comparative Example

The mixture from Example 3 was heated at 40° C. with stirring for 120 minutes. A solution of Latanoprost with concentration 0.00407% (w/v, or 81.4% of target concentration 0.005%) was obtained.

Example 5

Dexamethasone (104.05 mg) was dissolved in acetonitrile (5 mL). 1 mL of this solution was added to 545 mg of $NaH_2PO_4*H_2O$ and the mixture was dried in a reduced pressure for 15 hours. 20 mL of water were added and mixture was stirred. A fine suspension of dexamethasone (concentration about 0.1% w/v) was obtained.

We claim:

1. A method for preparing a ready-to-dissolve or ready-to-disperse composition of a difficult to dissolve in water compound comprising preparing a solution of at least one difficult to dissolve in water compound in at least one organic solvent; covering the surface of at least one substrate with the solution to form a matrix, wherein the substrate is insoluble in the at least one organic solvent but is soluble in water; and wherein the substrate is selected from the group consisting of ascorbic acid, boric acid, citric acid, salts of edetic acid, paraben esters, potassium or sodium lauryl sulfate, potassium or sodium salts of hydrohalogenic acids, potassium or sodium salts of phosphoric acid, benzalkonium chloride, sugars, ringer lactate and mixtures thereof; and removing the solvent to form a solid matrix.

2. The method according to claim 1, wherein the organic solvent is volatile.

3. The method according to claim 2, wherein the volatile organic solvent is a $C_1$-$C_6$ alcohol, acetonitrile, a $C_3$-$C_4$ ketone, a $C_1$-$C_3$ halogenated solvent, a $C_3$-$C_4$ ester, or a $C_5$-$C_8$ hydrocarbon.

4. The method according to claim 3, wherein the solvent is ethanol or acetonitrile.

5. The method according to claim 1, wherein the substrate is selected from the group consisting of ascorbic acid, boric acid, citric acid, edetate calcium disodium, edetate disodium, methyl paraben, ethyl paraben, sodium lauryl sulfate, sodium hydrogen phosphate, sodium phosphate, sodium dihydrogen phosphate, sodium chloride, sodium bromide, sodium iodide, benzalkonium chloride, potassium chloride, potassium bromide, potassium iodide, potassium hydrogen phosphate, potassium phosphate, potassium dihydrogen phosphate, sucrose, fructose, lactose, dextrose, ringer lactate and mixtures thereof.

6. The method according to claim 1, wherein the substrate is $NaH_2PO_4$ or $Na_2HPO_4$.

7. The method according to claim 1, wherein the removing step is performed under reduced pressure.

8. The method according to claim 1, wherein the difficult to dissolve in water compound is dexamethasone, fluticasone, hydrocortisone, latanoprost, mometasone, or travoprost.

9. The method according to claim 1, wherein the difficult to dissolve in water compound is latanoprost.

10. A method for preparing an aqueous solution or suspension of difficult to dissolve in water compound comprising preparing a solid matrix by the method of claim 1 and combining the solid matrix with a sufficient amount of water to form an aqueous solution or suspension of the difficult to dissolve compound.

11. The method according to claim 10, wherein the amount of water is sufficient to form an aqueous solution.

12. The method according to claim 10, wherein the amount of water is sufficient to form a suspension.

13. The method according to claim 10, wherein the amount of water is sufficient to form a saturated aqueous solution.

14. The method according to claim 10, further comprising adding at least one additional compound selected from the group consisting of buffers, coloring agents, emulsifying agents, flavoring agents, preservatives, solubilizers, surfactants, suspending agents, tonicity agents, and viscosity agents.

15. The method according to claim 14, wherein the additional compound is benzalkonium chloride or sodium chloride.

16. The method according to claim 14, wherein the additional compound is added to the aqueous solution or suspension.

17. The method according to claim 3, wherein the $C_5$-$C_8$ hydrocarbon is a pentane or a hexane.

* * * * *